(12) United States Patent
Feng

(10) Patent No.: US 12,065,531 B2
(45) Date of Patent: Aug. 20, 2024

(54) POLYGLYCOLIC ACID RESIN AND PRODUCTION PROCESS THEREOF

(71) Applicant: Pujing Chemical Industry Co., Ltd., Shanghai (CN)

(72) Inventor: Lei Feng, Shanghai (CN)

(73) Assignee: Pujing Chemical Industry Co., Ltd., Shanghai (CN)

( * ) Notice: Subject to any disclaimer, the term of this patent is extended or adjusted under 35 U.S.C. 154(b) by 689 days.

(21) Appl. No.: 17/289,407

(22) PCT Filed: Oct. 29, 2018

(86) PCT No.: PCT/CN2018/112475
§ 371 (c)(1),
(2) Date: Apr. 28, 2021

(87) PCT Pub. No.: WO2020/087222
PCT Pub. Date: May 7, 2020

(65) Prior Publication Data
US 2022/0010052 A1  Jan. 13, 2022

(51) Int. Cl.
| | | |
|---|---|---|
| C08G 18/42 | (2006.01) |
| B29C 45/00 | (2006.01) |
| B29K 67/00 | (2006.01) |
| C07C 31/22 | (2006.01) |
| C07C 31/24 | (2006.01) |
| C08G 18/73 | (2006.01) |
| C08G 18/79 | (2006.01) |
| C08G 63/06 | (2006.01) |
| C08G 63/685 | (2006.01) |
| C08G 63/82 | (2006.01) |
| C08G 63/91 | (2006.01) |

(52) U.S. Cl.
CPC ...... *C08G 18/4266* (2013.01); *B29C 45/0001* (2013.01); *C07C 31/22* (2013.01); *C07C 31/24* (2013.01); *C08G 18/73* (2013.01); *C08G 18/797* (2013.01); *C08G 63/06* (2013.01); *C08G 63/6852* (2013.01); *C08G 63/823* (2013.01); *C08G 63/912* (2013.01); *B29K 2067/04* (2013.01); *Y02W 90/10* (2015.05)

(58) Field of Classification Search
CPC .. C08G 18/4266; C08G 18/73; C08G 18/797; C08G 63/06; C08G 63/6852; C08G 63/823; C08G 63/912; B29K 2067/04
See application file for complete search history.

(56) References Cited

U.S. PATENT DOCUMENTS

| | | |
|---|---|---|
| 2003/0125431 A1 | 7/2003 | Yamane et al. |
| 2004/0106734 A1 | 6/2004 | Rose |
| 2006/0255495 A1 | 11/2006 | Yamane et al. |
| 2014/0024769 A1* | 1/2014 | van Walsem .......... C08G 63/06 562/580 |
| 2015/0290858 A1 | 10/2015 | Okura et al. |
| 2016/0060387 A1 | 3/2016 | Gadda et al. |

FOREIGN PATENT DOCUMENTS

| | | |
|---|---|---|
| CN | 101296994 A | 10/2008 |
| CN | 101717499 A | 6/2010 |
| CN | 105154058 A | 12/2015 |
| JP | 2012012560 A | 1/2012 |
| JP | 2014139265 A | 7/2014 |
| JP | 2016006141 A * | 1/2016 |
| JP | 2016006141 A | 1/2016 |
| TW | 200815497 A | 4/2008 |

OTHER PUBLICATIONS

Extended European Search Report from counterpart European U.S. Application No. 18938898, dated May 23, 2022, 11 pages.
PCT International Search Report and Written Opinion, PCT/CN2018/112475, Jun. 28, 2019, 10 pages.
China Patent Office, Chinese Application No. 201880053022, First Office Action and Search Report and translation thereof mailed Jun. 30, 2022, 37 pages.

* cited by examiner

*Primary Examiner* — Marc S Zimmer
*Assistant Examiner* — Surbhi M Du
(74) *Attorney, Agent, or Firm* — Quarles & Brady LLP

(57) ABSTRACT

Disclosed is a branched polymer resin comprising repeating units of —(—OCH2-CO—)— or —(—CO—CH2O—)—, which is produced by ring-opening polymerization in the presence of structure regulators and optionally end-capping agents. The branched polymer resin exhibits a lower melt viscosity and a higher heat-stable temperature and suitable for melt processing.

11 Claims, No Drawings

POLYGLYCOLIC ACID RESIN AND PRODUCTION PROCESS THEREOF

CROSS-REFERENCE TO RELATED APPLICATIONS

This application represents the U.S. national stage entry of International Application No. PCT/CN2018/112475 filed Oct. 29, 2018, the disclosure of which is incorporated herein by reference in its entirety and for all purposes.

FIELD OF THE INVENTION

The present invention relates to a novel structure of polyglycolic acid (PGA) resin obtained by ring-opening polymerization, and preparation thereof.

BACKGROUND OF THE INVENTION

The aliphatic polyester is a high molecular weight polymer containing an aliphatic ester bond in a molecular chain, and has a polyhydroxylic fatty acid skeleton as a main structure of a molecular chain. It can be biodegraded by microorganisms or enzymes in nature such as soil or ocean. Examples of such a degradable polymer material include a polyhydroxybutyric acid synthesized biologically, and polylactic acid, polyglycolic acid (PGA), polycaprolactone, or the like obtained by chemical synthesis. Since some aliphatic polyesters participate in the tricarboxylic acid cycle and metabolized in a living body. Since 1960s, biodegradable aliphatic polyesters have been used in surgical sutures, postoperative anti-adhesion membrane and artificial organs. It is widely used in biomedical fields such as drug controlled release carriers (CN1537144A). At the same time, such materials are widely used for packaging materials such as films, sheets and bottles having a single layer or a multilayer structure due to their excellent biodegradability to reduce white pollution. In particular, the PGA resin has superior performance in heat resistance, gas barrier properties, mechanical strength, etc. compared to other biodegradable aliphatic polyester materials, and thus is widely used for sheets, films, and containers and injection molded articles (CN1863664A).

The molten PGA resin is characterized in that its melting temperature is about 220° C. This shows that the PGA resin has excellent heat resistance characteristics. However, since the melt viscosity of the PGA is high, high temperature and high pressure are required for injection molding. This sometimes results in deformation of the molded PGA resin molded articles. When it is compounded with other resins, the molten PGA fluid also causes deformation of other synthetic resin molded articles in the mold.

Therefore, in order to ensure good flowability of the PGA resin during melt processing, especially for a complicated molding or molding requiring a precise size, it is generally required to increase the melt processing temperature to 260-320° C., Such a high processing temperature is followed by a series of problems such as thermal degradation of the PGA resin, coloration of the molded article, and deterioration of the mechanical strength of the resulting product.

In the past research on processing of PGA resins, in order to avoid the negative effects such as coloring and thermal degradation caused by excessive processing temperature, blending modification or copolymerization modification is usually used to improve the melt rheological behavior of a PGA resin in order to reduce processing temperature. However, both of these methods rely heavily on introduction of a large amount of modifiers or copolymer components such that the properties of the PGA host polymer itself such as gas barrier properties are completely changed.

It is desirable to develop a PGA resin material excellent in flowability at the time of melt molding while maintaining the properties of the PGA itself. Chinese patent CN 104640684 discloses a cured extrusion molding of a PGA resin, which is extruded in a mold channel at 240-285° C. by optimizing curing extrusion molding conditions. Chinese patent CN02825936X discloses a PGA resin having improved thermal properties such as crystallinity, which is prepared by a thermal history of PGA Tm+38° C. to a temperature higher than Tm+70° C. The melting granulation temperature of the crystalline PGA resin can be lowered to 250° C.

There remains a need for a PGA-based polymer having a lower melt viscosity and a higher heat-stable temperature and suitable for melt processing.

SUMMARY OF THE INVENTION

The present invention provides a polymer resin (or a polyglycolic acid (PGA) resin) of a novel structure and preparation thereof by ring-opening polymerization.

A polymer resin is provided. The polymer resin comprises one or more repeating units of —(—OCH$_2$—CO—)— or —(—CO—CH$_2$O—)— and one or more bonding units. Each bonding unit is selected from the group consisting of:

(a) bonding unit 1 is,

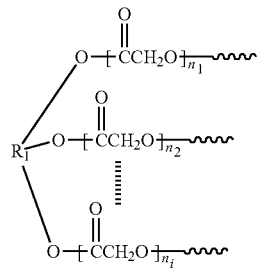

(b) bonding unit 2 is

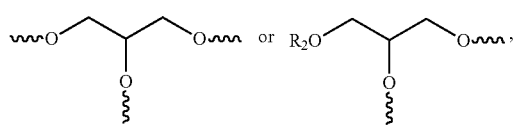

(c) bonding unit 3 is

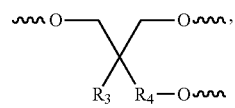

(d) bonding unit 4 is

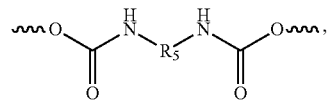

and (e) bonding unit 5 is

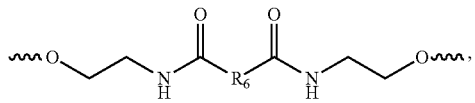

∽∽∽ is a polymer segment consisting of a plurality of the repeating unit of —(—OCH$_2$—CO—)— or —(—CO—CH$_2$O—)—. R1, R2, R3, R4, R5 and R6 are each an aliphatic or aromatic group.

Bonding unit (a) may have 3-20, preferably 3-6, arms, and each arm (i.e., each of $n_1$, $n_2$ . . . $n_i$) may have 1-2,000, preferably 10-1,000, repeating units of —(—OCH$_2$—CO—)— or —(—CO—CH$_2$O—)—.

Each bonding unit may be linked with a repeating unit or another bonding unit via a bond, preferably a covalent bond.

The polymer resin may have a mean-square radius of gyration of 10-80 nm as measured in hexafluoroisopropanol at 25° C.

The polymer resin may be prepared by ring-opening polymerization of a cyclic monomer in a molten state in the presence of a structure regulator.

The polymer resin may be prepared by ring-opening polymerization of a cyclic monomer in a molten state in the presence of a structure regulator and an end-capping agent.

The cyclic monomer may be a cyclic compound capable of undergoing ring-opening polymerization. Examples of the cyclic monomers include lactides, 4-8 carbon lactones, p-dioxanone, and trimethylene carbonate. The structure regulator may have the structural formula of $M_x$-R—$N_y$, ($2 \leq x+y \leq 20$), wherein M and N are each OH, —NH$_2$, —N=C=O, —C(O)Cl, o-dianhydride, oxazoline, epoxy or oxetane, and R is an aliphatic or aromatic group. The end-capping agent may be a carbodiimide compound.

The polymer resin may have a melt viscosity of 30-1200 Pa·s as measured at a temperature of 225° C. and a shear rate 100 s$^{-1}$, a thermal stable temperature above 280° C., and Grade A of injection molding grade at 240° C.

For each polymer resin of the invention, a process of preparing the polymer resin is provided. The process may comprise ring-opening polymerizing a cyclic monomer in a molten state in the presence of a structure regulator. The process may comprise ring-opening polymerizing a cyclic monomer in a molten state in the presence of a structure regulator and an end-capping agent. The process may comprise (a) mixing a cyclic monomer with a catalyst, an initiator and a structure regulator A in a prepolymerization reactor at a temperature above the melting temperature of the cyclic monomer and below the melting temperature of the polymer resin, whereby a melted prepolymerization composition is formed; (b) polymerizing the melted prepolymerization composition in the presence of a structure regulator B, whereby a melted polymerization composition is formed; and (c) optimizing the melted polymerization composition, whereby the melted PGA resin is formed.

The process may further comprise molding the melted polymer resin to make a PGA product.

According to the process on the invention, the cyclic monomer may be a cyclic compound capable of undergoing ring-opening polymerization. Examples of the cyclic monomers include lactides, 4-8 carbon lactones, p-dioxanone, and trimethylene carbonate. The structure regulator may have the structural formula of $M_x$-R—$N_y$ ($2 \leq x+y \leq 20$), wherein M and N—are each OH, —NH$_2$, —N=C=O, —C(O)Cl, o-dianhydride, oxazoline, epoxy or oxetane, and R is an aliphatic or aromatic group. The end-capping agent may be a carbodiimide compound.

DETAILED DESCRIPTION OF THE INVENTION

A primary object of the present invention is to provide a novel polymer resin containing a —(—OCH$_2$—CO—)— or —(—CO—CH$_2$O—)— repeating unit and a structure regulator bonding unit, and a process for producing the same.

One of the objects of the present invention is to provide a polymer resin which is prepared by ring-opening polymerization of a cyclic monomer in a molten state in the presence of a structure regulator, wherein the polymer resin has a mean-square radius of gyration of 10-80 nm as measured in hexafluoroisopropanol at 25° C.

The invention provides a polymer resin comprising one or more repeating units of —(—OCH2-CO—)— or —(—CO—CH$_2$O—)— and one or more bonding units each selected from the group consisting of:

(a) bonding unit 1 is,

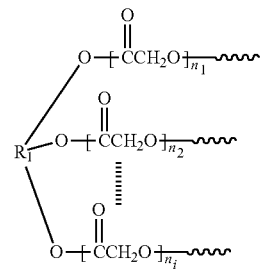

(b) bonding unit 2 is

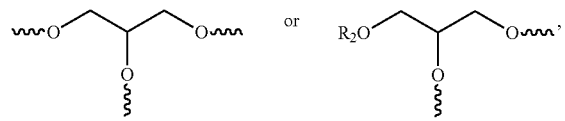

(c) bonding unit 3 is

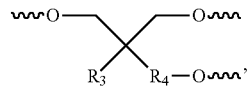

(d) bonding unit 4 is

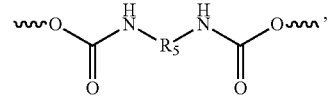

(e) bonding unit 5 is

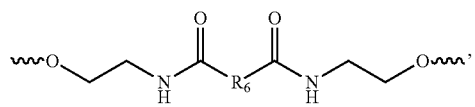

wherein:
- ⁓⁓⁓ is a polymer segment consisting of a plurality of the repeating unit of —(—OCH$_2$—CO—)— or —(—CO—CH$_2$O—)—; R1, R2, R3, R4, R5 and R6 are each an aliphatic or aromatic group. Each of the structure of bonding units may be derived from a residue of a structure regulator used in ring-opening polymerization process.

Bonding unit (a) may have 3-20, preferably 3-6, arms, and each arm (i.e., each of $n_1$, $n_2$ . . . $n_t$) may have 1-2,000, preferably 10-1,000, repeating units of —(—OCH$_2$—CO—)— or —(—CO—CH$_2$O—)—.

Each bonding unit may be linked with a repeating unit or another bonding unit via a bond, preferably a covalent bond.

The polymer resin may have a mean-square radius of gyration of 10-80 nm as measured in hexafluoroisopropanol at 25° C.

From the mechanism of ring-opening polymerization, a structure regulator of the present invention plays an important role in the formation of a multi-branched macromolecular structure in the polymer resin. The structure regulator may have the structural formula $M_x$-R—$N_y$ ($2 \leq x+y \leq 20$), in which M and N may be —OH, —NH$_2$, —N=C=O, —C(O)Cl, o-dianhydride, oxazoline, epoxy, oxetane, or a combination thereof, preferably —OH, —N=C=O, oxazoline, epoxy, oxetane or a combination thereof, and R may be an aliphatic or aromatic group.

According to the present invention, one or more structure regulators may be added to one or more steps in the ring-opening polymerization process. For example, different structure regulators may be added into the same step of polymerization process, or the same structure regulator may be added into different steps of polymerization process. The present invention employs two types of structure regulators which are introduced into the polymerization process at different steps. The total amount of the structure regulators may be from about 0.01 wt % to about 5 wt % relative to the monomer (e.g., glycolide).

The mean-square radius of gyration as measured in hexafluoroisopropanol at 25° C. may be used to characterize the macromolecular coil size of the branched polymer resin (e.g., PGA resin) and the branching effect of the structure regulator.

The polymer resin of this invention comprising repeating units of —(—OCH$_2$—CO—)— or —(—CO—CH$_2$O—)— may have a branched macromolecular structure formed by a structural fragment introduced by a structure regulator. The mean-square radius of gyration of such a polymer resin as measured in hexafluoroisopropanol at 25° C. may be reduced significantly, as compared with a corresponding linear polymer resin having an equal amount of repeating units of —(—OCH$_2$—CO—)— or —(—CO—CH$_2$O—)—.

Based on the production process of the branched polymer resin (e.g., PGA resin), the branched polymer resin (e.g., PGA resin) has a mean-square radius of gyration of about 10-80 nm, 20-70 nm, 25-65 nm, 10-50 nm or 40-50 nm, preferably about 20-70 nm, more preferably about 25-65 nm, as measured in hexafluoroisopropanol at 25° C.

One of the objects of the present invention is to provide a polymer resin (e.g. PGA resin) which is excellent in melt flowability, excellent in melt stability, and excellent in melt processability, and a production process thereof. And, the melt flowability of a polymer resin may be characterized by its melt viscosity; the melt stability of a polymer resin may be characterized by its thermal stable temperature; the melt processability of the polymer resin may be characterized by its injection molding grade.

It is known that the melt viscosity of polymer materials comes from the interaction among the molecules in the polymer, such as internal friction, diffusion, molecular chain orientation, entanglement, etc., which contributes to the resistance of polymer melt flow. Reducing the entanglement among macromolecular chains, reducing the internal friction among macromolecules, and reducing the interaction among macromolecular chains decrease melt viscosity of the macromolecules.

The inventors have conducted intensive studies of preparing a PGA resin having a low melt viscosity and have introduced a branched structure into a linear PGA to improve the interaction among the macromolecules of a PGA resin. This branched structure may inhibit the internal friction and the entanglement among macromolecular chains and decrease the melt viscosity, which in turn fundamentally changes the melt rheological behavior of the PGA resin.

The inventors have surprisingly found that introducing a structure regulator in an amount less than 2 wt % based on the total weight of the materials used for ring-opening polymerization of glycolide converted a linear PGA into a branched PGA, which had much better melt flowability than a corresponding linear PGA having an equal amount of repeating units of —(—OCH$_2$—CO—)— or —(—CO—CH$_2$O—)—.

Compared with a corresponding linear polymer resin (e.g., PGA resin) of the same process, a branched polymer resin (e.g., PGA resin) may cause a decrease in the size of the polymer (e.g., PGA) coil due to a structural change of the branched structure caused by a structure regulator, thereby improving its melt viscosity. Specifically, the capillary melt viscosity of the branched polymer resin (e.g., PGA resin) is in the range of about 30-1200 Pa·s at 225° C. and the shear rate of 100 s$^{-1}$.

It is well known that the melting temperature of PGA is about Tm=220° C. Generally, melt viscosity can be reduced by increasing the test temperature to above Tm+30° C. and increasing the shear rate to above 400/s. However, the inventors have surprisingly found that the decrease in melt viscosity obtained in the above case is actually caused by a large decrease in the molecular weight of the PGA resin caused by thermal degradation. In order to avoid any influence of thermal degradation on the melt viscosity test, the melt viscosity of the branched PGA resin is measured at a temperature near the melting point of the PGA resin (e.g., 225° C.) and a low shear rate of 100 s$^{-1}$.

The branched polymer resin (e.g., PGA resin) having satisfactory melt processability may have a melt viscosity of about 30-1200 Pa-s, preferably 50-800 Pa-s, more preferably 70-400 Pa·s, measured by a capillary rheometer (capillary diameter 1 mm, length 16 mm) with a cylinder (diameter 15 mm and length 290 mm) at a temperature of 225° C. and a shear rate 100 s$^{-1}$.

The inventors have also surprisingly found that adding a structure regulator further improved the melt stability of the branched PGA without changing the polymerization process as compared with the linear PGA.

The branched polymer resin (e.g., PGA resin) of the present invention has more excellent melt stability than the corresponding linear polymer resin (e.g., PGA resin) of the same process. The melt stability described in the present invention is defined as the thermal temperature corresponding to a weight loss of 3% on the thermogravimetric curve of the polymer sample. Among them, the thermogravimetric curve is obtained by taking a polymer sample of about 10 mg, heating in a nitrogen atmosphere (nitrogen flow rate 10 ml/min), heating from 40° C. to 400° C., and a heating rate of 10° C./min. The curve of residual weight of polymer sample with temperature is determined.

The branched polymer resin (e.g., PGA resin) of the present invention may have a 3% weight loss at 280° C. or higher, preferably 290° C. or higher, due to the use of a structure regulator and/or an end-capping agent.

Compared with a corresponding linear polymer resin of the same process, the branched polymer resin (e.g., PGA resin) of the present invention has a lower melt viscosity and higher degradation temperature. Under the same processing temperature, the branched polymer resin (e.g., PGA resin) has a much lower melt viscosity than a corresponding linear polymer. To achieve the same melt viscosity, the branched polymer resin (e.g., PGA resin) requires a melt temperature more close to the melting point of the polymer (e.g., PGA) than a corresponding linear polymer resin.

Injection molding grade of the polymer resin (e.g., PGA resin) may be used for a comprehensive evaluation of the improved melt processability brought by its branched structure. Specifically, the molten polymer resin (e.g., PGA resin) may be injected into a mold of two cone-column structures connected in series. Based on the filling and molding of the first and second cone-column structures by the molten polymer resin, the polymer resin (e.g., PGA resin) may be classified into three grades: A, B and C. The branched polymer resin (e.g., PGA resin) of the present invention can achieve a Grade A (injection molding grade) in addition to good melt flowability and thermal stability under the test conditions and shows further reduced processing window (about 240° C.) due to the decrease of the decomposition temperature.

The PGA resin is produced and manufactured by a process of continuous ring-opening polymerization of glycolide, maintaining the melt state throughout the whole polymerization, modification and molding integration process.

One of the objects of the present invention is to provide a polymerization, modification and molding integrated manufacturing process for obtaining forementioned polymer resin on a large scale continuously.

In order to avoid the impact of the high heat history of a PGA resin on physicochemical properties of a secondary modification and molding process, this invention provides a continuous ring-opening polymerization, modification and molding integration process of glycolide to achieve continuous industrial production of PGA resin by using a structure regulator to improve the melt flowability and processing window of the PGA resin.

In addition, in order to solve the heterogeneity of the quality of the PGA resin produced by an indirect reaction device, the present invention utilizes an existing reaction device to combine and realize the synergistic effect of the characteristics between different devices. The continuous industrial production of PGA resin is achieved and the resulting product has stability and uniformity. A kettle reactor, a tubular reactor, a plug flow reactor or a combination thereof may be used to form a set of process equipment for integrating polymerization, modification and molding of the PGA resin. The kettle reaction system includes a vertical reactor, a horizontal self-cleaning reactor and the like; the plug flow reaction extrusion system includes a single-screw reaction unit, a twin-screw reaction unit, and the like. The tubular reaction system includes a static mixer such as a SK type static mixer, an SV type static mixer, and an SX type static mixer.

The present invention is to provide a polymerization, modification and molding integrated manufacturing process, which description is as follows:

a) Prepolymerization Step

In the prepolymerization step, a kettle reactor, a plug flow reactor or a tubular reactor is used as a prepolymerization reactor. A monomer (e.g., glycolide), a catalyst, a structure regulator A, and optionally an initiator, are injected into the prepolymerization reactor through a weightless weighing or metering pump. The prepolymerization reaction is carried out at a temperature above the melting point (TmGL ° C.) of the monomer (e.g., glycolide), preferably TmGL+20° C., more preferably TmGL+40° C., and below the melting temperature (Tm ° C.), preferably Tm−20° C., and more preferably Tm−40° C. of the polymer to form a prepolymerization composition in the prepolymerization reactor. The reaction time is from about 1 min to about 5 h, preferably from about 5 min to about 4 h, preferably from 10 min to 3 h. A prepolymerization composition obtained by the prepolymerization reaction is advanced to the polymerization reaction step by melt transport.

b) Polymerization Step

In the polymerization step, the prepolymerization composition feeds into a polymerization reactor by melt transport. The polymerization reactor may be a kettle reactor, a plug flow reactor or a tubular reactor. Further chain growth of the prepolymerization composition can be achieved by adjusting the polymerization conditions such as the polymerization temperature, time and pressure. A structure regulator B may be added to further regulate the resulting structure of the polymer. The polymerization temperature is in the range from Tc+10° C. or more to Tm+37° C. or less. Tc is the crystallization temperature of the polymer. Tm is the melting temperature of the polymer. The polymerization time may be from about 1 min to about 72 h, preferably 5 min to 48 h, and more preferably 10 min to 24 h. The polymerization system pressure (absolute pressure) may be about $0.5\text{-}10^{-6}$ MPa. The upper limit of the system pressure (absolute pressure) is 0.5 MPa, preferably 0.2 MPa, further preferably 0.1 MPa, and the lower limit is $10^{-6}$ MPa, preferably $10^{-4}$ MPa, still more preferably $10^{-2}$ MPa. As a result, a polymerization composition is formed in the polymerization reaction.

c) Optimization Step

In the optimization step, the polymerization composition feeds into an optimization reactor by melt transport. The optimization reactor may be a kettle reactor, a plug flow reactor or a tubular reactor. The main process of the optimization reaction is devolatilization and modification of the polymerization composition. The modifier may be selected from the group consisting of an antioxidant (including but not limited to phenolic antioxidants, amine antioxidants, thioester antioxidants, phosphite antioxidants or a combination thereof), a metal deactivator (including but not limited to MD24, Chel-180, XL-1, CDA10, CDA6 or a combination thereof), a hydrolysis inhibitor, a light stabilizer (including but not limited to benzophenones, benzotriazoles, hindered amines, or a combination thereof), and an inorganic filler (including but not limited to glass, carbon, carbon nanotubes, talc, calcium carbonate or a combination thereof). The modifier may be an end-capping agent. Optimization may be achieved by adjusting the temperature, rotation speed and vacuum of the reaction system. The optimization reaction temperature may be in the range from Tm to Tm+37° C. Tm is the melting temperature of the polymer. The upper limit of the reaction temperature may be Tm+37° C., preferably Tm+20° C., more preferably Tm+10° C. The lower limit of the reaction temperature may be Tc+20° C., preferably Tc+30° C., more preferably Tc+40° C. The screw rotation speed may be about 1-500 rpm. The upper limit of the rotation speed may be preferably 300 rpm, more preferably 200 rpm. The lower limit may be preferably 25 rpm, more preferably 50 rpm. Vacuum degree (absolute pressure) of the optimization reaction system ranges from about 1 Pa to normal pressure, preferably from 1 to 5000 Pa, and more preferably from 1 to 100 Pa. The optimization reaction time may be from about 1 min to about 24 h, preferably from 5 min to 12 h, and further preferably from 10 min to 6 h. After the optimization step, the polymer resin is obtained.

d) Molding Step

The polymer resin may be molded into a polymer product (e.g., PGA product). The strip die of the optimization reactor outlet may be replaced with a mold assembly corresponding to a downstream product such as an underwater pellet die and assembly, a calendering film die and assembly, a cast film die and assembly, a blown film die and assembly, a fiber spinning die and assembly, or a rod extrusion, tube extrusion die and assembly and sheet extrusion die and assembly to achieve different molding requirements. A product made by molding the polymer resin of the present invention may maintain the stability and uniformity of the physical and chemical properties of the polymer (e.g., PGA) to the utmost extent.

The materials covered by the present invention include the following:

1. Monomer

The monomer may be a lactide obtained by cyclization of bimolecular hydroxycarboxylic acid. Examples of the hydroxycarboxylic acids include glycolic acid, lactic acid (L, D or DL), α-hydroxybutyric acid, α-hydroxyvaleric acid, α-hydroxyisobutyric acid, α-hydroxycaproic acid, α-hydroxyisohexanoic acid, α-Hydroxyheptanoic acid, α-hydroxyoctanoic acid, α-hydroxydecanoic acid, α-hydroxymyristic acid and α-hydroxystearic acid. The monomer may also be selected from the group consisting of 4-8 carbon lactones, p-dioxanone, trimethylene carbonate and other cyclic compounds that can undergo ring-opening polymerization. Glycolide, lactide, p-dioxanone, trimethylene carbonate and caprolactone are preferred. Glycolide, lactide and p-dioxanone are particularly preferred. Glycolide is most preferred.

2. Catalyst

The catalyst may be any metal catalyst for ring-opening polymerization of a cyclic ester or a lactide. The metal catalyst may be a fatty acid salt, a carbonate, a sulfate, a phosphate, an oxide, a hydroxide, a halide, or an alkoxide of at least one metal selected from the group consisting of tin, aluminum, zinc, calcium, titanium, magnesium, and a rare earth element. In particular, examples of the tin-containing compound include stannous chloride, stannous octoate, tin tetrachloride, tin oxide, tin myristate, tin octylate, tin stearate, tetraphenyl tin, methanol tin, ethanol tin, butanol tin, and the like. Examples of the aluminum-containing compound include alumina, aluminum acetylacetonate, aluminum isopropoxide, and an aluminum-imine complex. The catalyst is preferably a tin-based catalyst, more preferably tin tetrachloride or stannous octoate. The catalyst may be in the amount of about 0.0001-2 wt %, preferably 0.001-0.5 wt %, more preferably 0.01-0.1 wt %, based on the weight of the glycolide.

3. Structure Regulator

The structure regulators of the present invention may be classified into two classes, namely, a structure regulator A and a structure regulator B, according to the step in which it plays a branching role in the ring-opening polymerization process.

The structure regulator A may be added during the chain growth phase of the ring-opening polymerization process, specifically during the polymerization, modification and molding integration process of the polymer resin (e.g. PGA resin). The structure regulator A may be added in the prepolymerization reaction step and the polymerization reaction step, preferably in the prepolymerization reaction step in an amount of about 0.001-5.000 wt %, preferably 0.01-1.00 wt %, relative to the monomer (e.g., glycolide).

As previously mentioned, structurally, M and N of the structure regulator A are preferably —OH, epoxy, oxetane or a combination thereof. Specifically, the structure regulator A is preferably an oxetane compound, a glycidyl compound, or an aliphatic polyol.

The oxetane compound has structure as follows:

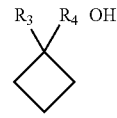

R3 represents an H, an alkyl group, an aryl group or an aralkyl group of C1-C4; and R4 represents a C1-C4 alkylene group. The alkyl group may, for example, be a methyl group, an ethyl group, a propyl group, an isopropyl group, a butyl group, an isobutyl group, a sec-butyl group or a t-butyl group, preferably a methyl group or an ethyl group. Examples of the alkylene group include a methylene group, an ethylene group, a trimethylene group, a propylene group, a tetramethylene group, an ethylethylene group, and a methyltrimethylene group, preferably a methylene group. Therefore, the oxetane structure regulator is most preferably 3-methyl-3-hydroxymethyloxetane or 3-ethyl-3-hydroxymethyloxetane.

The glycidyl compound may be glycidol, ethylene glycol monoglycidyl ether, propylene glycol monoglycidyl ether, neopentyl glycol monoglycidyl ether, trimethylolpropane monoglycidyl ether, trimethylolpropane diglycidyl ether, pentaerythritol monoglycidyl ether, pentaerythritol diglycidyl ether, pentaerythritol triglycidyl ether or a combination thereof, preferably glycidol.

The structure regulator A may be an aliphatic polyol, for example, trihydroxymethyl ethane, trihydroxymethyl propane, hexanetriol, butyltriol, pentylenetriol, decatriol, cyclohexanetriol, heptanetriol, octanetriol, pentaerythritol, butyltetraol, dipentaerythritol, glycerol, glycerol multimer, xylitol, mannitol, sorbitol, maltitol, galactitol, cyclohexanol, or a combination thereof, preferably trimethylolethane, trimethylolpropane, pentaerythritol, dipentaerythritol, and cyclohexahexaol, more preferably trishydroxymethyl ethane, trimethylol propane, and pentaerythritol.

The structure regulator B may be added to the polymerization reaction in the chain adjustment stage, specifically in the polymerization, modification and molding integration process of the above polymeric resin (e.g., polyglycolic acid resin). The structure regulator B may be added in the polymerization reaction step and the optimization reaction step, preferably in the polymerization reaction step in an amount of about 0.001-5.000 wt %, preferably 0.01-1.00 wt %, relative to the monomer (e.g., glycolide).

As described above, structurally, M and N of the B are preferably —N=C=O, oxazoline or a combination thereof. The structure regulator B may be a diisocyanate compound or a bisoxazoline compound. The diisocyanate compound may be a diisocyanate having 4 to 20 carbon atoms or a mixture thereof. Examples of commonly used diisocyanates include aliphatic diisocyanates such as tetramethylene diisocyanate, hexamethylene diisocyanate, octamethylene diisocyanate, decamethylene diisocyanate, dodecamethylene diisocyanate, fourteen methylene diisocyanate, trimethyl hexane diisocyanate; alicyclic diisocyanate such as 1,4-, 1,3- or 1,2-diisocyanate cyclohexane, 4,4'- or 2,4'-bis(isocyanatecyclohexyl)-methane, 1-isocyanate-3,3,5-trimethyl-5-(isocyanatemethyl)cyclohexane (isophorone diisocyanate), 1,3- or 1,4-bis(isocyanatemethyl)cyclohexane, 2,4- or 2,6-diisocyanate-1-methylcyclohexane; aromatic diisocyanates such as 2,4- or 2,6-toluene diisocyanate and mixtures thereof, m- or p-xylylene diisocyanate, 2,4'- or 4,4'-diphenyl Methane diisocyanate and its isomer mixture, 1,3- or 1,4-phenylene diisocyanate, 1-chloro-2,4-phenylene diisocyanate, 1,5-naphthylene diisocyanate, diphenylene-4,4'-diisocyanate, 4,4'-diisocyanate-3,3'-dimethylbiphenyl, 3-methyldiphenylmethane-4,4'-diisocyanate, tetramethyl benzo-dimethyl diisocyanate, 1,4-diisocyanate benzene, diphenyl ether-4,4'-diisocyanate.

The structure regulator B of the present invention is preferably hexamethylene diisocyanate, 1,3-bis(isocyanatemethyl)cyclohexane, isophorone diisocyanate, 4,4'- or 2,4'-di(isocyanatecyclohexyl)-methane, more preferably isophorone diisocyanate and hexamethylene diisocyanate, particularly preferably hexamethylene diisocyanate.

In addition, as a structure regulator B, a bisoxazoline compound includes 1,4-bis(4,5-dihydro-2-oxazole)benzene and 1,3-bis(4,5-dihydro-2)-oxazole)benzene, 2,2'-bis(2-oxazoline), (S,S) or (R,R)-2,6-bis(4-isopropyl-2-oxazoline-2-yl)pyridine, (S,S) or (R,R)-2,6-bis(4-phenyl-2-oxazolin-2-yl)pyridine, (S,S) or (R, R)-2,2'-isopropylidene bis(4-phenyl-2-oxazoline), (S,S) or (R,R)-2,2'-isopropylidene bis (4-tert-Butyl-2-oxazoline), (S,S) or (R,R)-2,6-bis(4-isopropyl-2-oxazolin-2-yl)-p-xylene or a combination thereof.

The bisoxazoline structure regulator of the present invention is preferably 1,4-bis(4,5-dihydro-2-oxazole)benzene and 2,2'-bis(2-oxazoline), more preferably 2,2'-bis(2-oxazoline).

4. End-Capping Agent

An end-capping agent may be added during finishing stage of the ring-opening polymerization process, specifically in the polymerization, modification and molding integration process of the above polymer resin (e.g., PGA resin). The end-capping agent may be optionally be added in the optimization reaction step and the molding process step, preferably in the optimization reaction step, generally in an amount of about 0.01-5.00 wt %, preferably 0.1-1.0 wt %, relative to the monomer (e.g., glycolide).

The end-capping agent may be a carbodiimide compound. Specific examples include: dicyclohexylcarbodiimide, diisopropylcarbodiimide, dimethylcarbodiimide, diisobutylcarbodiimide, dioctylcarbodiimide, octyldecylcarbodiimide, di-tert-butylcarbodiimide, tert-isopropylidenecarbodiimide, dibenzylcarbodiimide, diphenylcarbodiimide, N-octadecyl-N'-Phenylcarbodiimide, N-benzyl-N'-phenylcarbodiimide, N-benzyl-N'-tolylcarbodiimide, di-o-toluoylcarbodiimide, di-p-toluoylcarbodiimide, bis(p-nitrophenyl)carbodiimide, bis(p-aminophenyl)carbodiimide, bis(p-hydroxyphenyl)carbodiimide, bis(p-chlorophenyl)carbodiimide, bis(o-chlorophenyl)carbodiimide, bis(o-ethylphenyl)carbodiimide, Bis (p-ethylphenyl)carbodiimide, bis(o-isopropylphenyl) carbodiimide, bis(p-isopropylphenyl)carbodiimide, bis(o-isobutylphenyl)carbodiimide, bis(p-isobutylphenyl) carbodiimide, bis(2,5-dichlorophenyl)carbodiimide, p-phenylenebis(o-toluoylcarbodiimide), p-phenylene bis (cyclohexylcarbodiimide), p-phenylene bis(p-chlorophenylcarbodiimide), 2,6,2',6'-tetraisopropyldiphenylcarbondiimine, hexamethylene bis(cyclohexylcarbodiimide), ethylene bis(phenylcarbodiimide), ethylene bis(cyclohexylcarbodiimide), bis(2,6-Dimethylphenyl)carbodiimide, bis(2, 6-diethylphenyl)carbodiimide, bis(2-ethyl-6-isopropylphenyl)carbodiimide, double 2-butyl-6-isopropylphenyl) carbodiimide, bis(2,6-diisopropylphenyl)carbodiimide, bis (2,6-di-tert-butylphenyl)carbodiimide, bis(2,4,6-trimethylphenyl)carbodiimide, bis(2,4,6-triisopropylphenyl) carbodiimide, bis(2,4,6-tributylphenyl)biphenylene, di-p-naphthylcarbodiimide, N-tolyl-N'-cyclohexylcarbodiimide and N-tolyl-N'-phenylcarbodiimide. The end-capping agent is preferably dicyclohexylcarbodiimide, diisopropylcarbodiimide, bis(2,6-diisopropylphenyl)carbodiimide, 2,6,2',6'-tetraisopropyldiphenylcarbodiimide. The end-capping agent is more preferably dicyclohexylcarbodiimide and diisopropylcarbodiimide because of their industrial availability.

In conclusion, the invention provides a polymer resin comprising one or more repeating units of —(—OCH$_2$—CO—)— or —(—CO—CH$_2$O—)— and one or more bonding units each selected from the group consisting of:

(a) bonding unit 1 is,

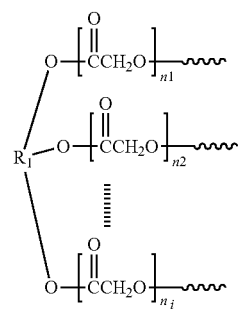

(b) bonding unit 2 is

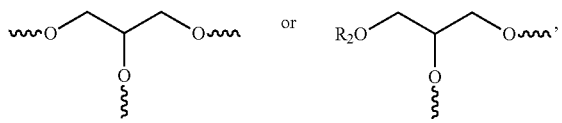

(c) bonding unit 3 is

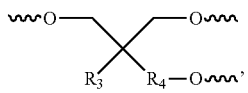

(d) bonding unit 4 is

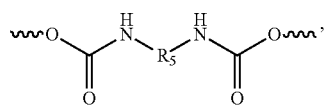

(e) bonding unit 5 is

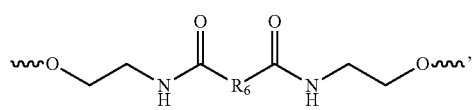

wherein:
~~~~ is a polymer segment consisting of a plurality of the repeating unit of —(—OCH$_2$—CO—)— or —(—CO—CH$_2$O—)—. Bonding unit (a) may have 3-20, preferably 3-6, arms, and each arm (i.e., each of n$_1$, n$_2$ ... n$_i$) may have 1-2,000, preferably 10-1,000, repeating units of —(—OCH$_2$—CO—)— or —(—CO—CH$_2$O—)—. R1 is a polyol residue, preferably a trimethylolethane, trimethylolpropane or pentaerythritol residue. R2 is a glycidyl ether residue, preferably a glycidol residue. R3 and R4 constitute oxetane residue, preferably a 3-methyl-3-hydroxymethyloxetane or 3-ethyl-3-hydroxymethyloxetane residue. R5 is a diisocyanate residue, preferably a hexamethylene diisocyanate residue. R6 is an oxazoline residue, preferably a 2,2'-bis(2-oxazoline) residue.

Each bonding unit may be linked with a repeating unit or another bonding unit via a bond, preferably a covalent bond.

The polymer resin may have a mean-square radius of gyration of 10-80 nm as measured in hexafluoroisopropanol at 25° C.

The terms covered by the present invention include the following:

The terms "polyglycolic acid (PGA)," "poly(glycolic acid) (PGA)" and "polyglycolide" are used herein interchangeably and refer to a polymer comprising repeating units of —(—OCH$_2$—CO—)— or —(—CO—CH$_2$O—)—. A polyglycolic acid may be prepared by polycondensation or ring-opening polymerization.

The term "structure regulator" used herein refers to an additive used in making the PGA to change the structure of the resulting PGA. One or more structure regulators may be used in the same or different steps of the PGA preparation process.

The term "end-capping agent" used herein refers to an additive used in making the PGA to block polymer chain extension.

The term "melt viscosity" as used herein refers to the viscosity of a molten polymer sample measured by a capillary rheometer (capillary diameter 1 mm, length 16 mm) with a cylinder (diameter 15 mm and length 290 mm) at a temperature of 225° C. and a shear rate 100 s$^{-1}$.

The term "thermal stable temperature" as used herein refers to the temperature corresponding to a weight loss of 3% on the thermogravimetric curve of the polymer sample. The thermogravimetric curve may be obtained by taking a polymer sample of about 10 mg, heating in a nitrogen atmosphere (nitrogen flow rate 10 ml/min), heating from 40° C. to 400° C., and a heating rate of 10° C./min. The curve of residual weight of polymer sample with temperature is determined.

The term "injection molding grade" as used herein refers to the degree of fullness of a test mold using an injection molding machine with nozzle temperature=240° C.; zone 1 temperature=220° C.; zone 2 temperature=230° C.; zone 3 temperature=235° C.; zone 4 temperature=240° C.; melting temperature=220° C. The test mold is a two cone-column structures in series connected tightly with each other. The first cone-column has a height of 0.5 cm, a bottom width of 5 cm and a cone height of 5 cm; the second cone-column has a height of 0.5 cm high, a bottom width of 2 cm and a cone height of 4 cm.

The term "significant increase" used herein refers to an increase of at least about 10%, 20%, 30%, 40%, 50%, 60%, 70%, 80%, 90%, 95% or 99%.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

The test methods covered by the present invention are as follows:

1. Monomer Conversion Rate

The monomer conversion rate is determined according to the following method: 1) 10 mg glycolide and 10 mg 1,4-butyrolactone (internal standard) are placed in a 50 ml volumetric flask. 30 ml hexafluoroisopropanol and 20 ml acetone are added into the flask to make a glycolide reference solution containing about 0.2 mg/ml of the glycolide and 0.2 mg/ml of the 1,4-butyrolactone. 2) 0.5 g of a sample is added into a container, which is closed tightly, and dissolved in 15 ml hexafluoroisopropanol in a water bath at 60° C. for 3-4 h. After the dissolution is completed, the test solution is transferred to a 100 ml round bottom (flat bottom) flask, and 15 ml hexafluoroisopropanol is added to the closed metal container for brushing before being transferred to a flask. 10 ml acetone is added to precipitate the polymer. Then, 10 mg 1,4-butyrolactone is added, shaken and dissolved the polymer precipitate before filtering. The filtrate is removed. 3) 1 μl of each of the reference solution and the test solution are injected into a gas chromatograph and the chromatogram is recorded. The residual monomer content W1 is calculated from the peak area, and 1-W1 is the monomer conversion.

2. Mean-Square Radius of Gyration

A mean-square radius of gyration (Zimm algorithm) is determined by using a laser light scattering instrument (helium/neon laser generator power: 22 mW) of the German ALV company CGS-5022F type. A polymer sample is dried to a constant weight in a vacuum oven at 50° C. Hexafluoroisopropanol (HPLC grade) is used as a solvent at 25° C. to prepare a polymer test solution having a concentration of $C_0$=0.001 g/g (polymer/hexafluoroisopropanol). Four concentrations $C_0$, ¾$C_0$, ½$C_0$ and ¼$C_0$ of the polymer/hexafluoroisopropanol solution are prepared by dilution and filtering through a 0.2 μm filter. The test wavelength is 632.8 nm; the scattering angle range is 15-150 degrees; and the test temperature is 25±0.1° C.

3. Melt Viscosity

The melt viscosity of a polymer is measured using a Malvern Rosand RH7 capillary rheometer (capillary diameter 1 mm, length 16 mm). Prior to testing, a polymer sample is dried to constant weight in a vacuum oven at 50° C. Approximately 20 g of the polymer sample is weighed into a cylinder having a diameter of 15 mm and a length of 290 mm at a set temperature of 225° C. After being kept molten for 5 min, the melt viscosity of the polymer sample is measured at a shear rate of 100 s$^{-1}$.

4. Thermal Stable Temperature

The thermal stable temperature of a polymer is measured using a German TG 209 F3 Tarsus type thermogravimetric analyzer. Prior to testing, a polymer samples is dried to constant weight in a vacuum oven at 50° C. About 10 mg of a polymer sample is taken, and the temperature is raised from 40° C. to 400° C. under a nitrogen atmosphere (nitrogen flow rate of 10 ml/min), and at a temperature rise rate of 10° C./min. The change in the weight of the residual sample is measured as the temperature went up. The term "thermal stable temperature" used herein refers to the temperature at which the polymer sample has a weight loss of 3 wt %.

5. Injection Molding Grade

The melt processability of the polymer resin in this invention is characterized by injection molding grade. The injection molding grade of a polymer is evaluated by Ningbo Haitian Group Haitian Tianxiang SaII injection molding machine. The temperature regime for injection molding is as follows: nozzle temperature=240° C.; zone 1 temperature=220° C.; zone 2 temperature=230° C.; zone 3 temperature=235° C.; zone 4 temperature=240° C.; melting temperature=220° C. The molten polymer resin is injected into a mold with two cone-column structures in series connected tightly with each other. The first cone-column mold has a height of 0.5 cm, a bottom width of 5 cm and a cone height of 5 cm. The second cone-column mold has a height of 0.5 cm high, a bottom width of 2 cm and a cone height of 4 cm. The injection molding grade of the polymer is evaluated according to the following criteria:
  A: The first cone-column mold and the second cone-column mold were each fully filled with complete molding;
  B: The first cone-column mold has relative good molding, but the end of the second cone-column mold has an unfilled space; and
  C: The first cone-column mold shows difficulties to form molding and had unfilled space.

Example 1. Polymers 1 and 2

Polymers 1-2 and Comparative 1 were prepared and evaluated for their mean-square radius of gyration, melt viscosity, thermal stable temperature and injection molding grade.

Comparative 1 was prepared by ring-open polymerization. 100 g of glycolide, 5 mg of tin tetrachloride (ring-opening polymerization catalyst) and 50 mg of lauryl alcohol (initiator) were placed in a glass test tube and polymerized at 200° C. for 3 hours. After polymerization, additional polymerization was carried out at 160° C. for 12 hours. After the additional polymerization, the resulting polymer was cooled, collected, and then pulverized and washed with acetone several times. Lastly, the polymer was dried under vacuum at 30° C. to a constant weight. As a result, Comparative 1 was obtained.

Polymer 1 was prepared in the same way as that for Comparative 1 except that 50 mg of glycidol (structure regulator A) was added in the polymerization.

Polymer 2 was prepared in the same way as that for Polymer 1 except that the additional polymerization was carried out at 160° C. for 10 hours and then 50 mg of hexamethylene diisocyanate (structure regulator B) was added to continue the additional polymerization for 2 more hours.

Polymers 1-2 and Comparative 1 were evaluated in the following tests and the results are shown in Table 1.

TABLE 1

Properties of Polymers 1 and 2

|  | Initiator | Structure Regulator A | Structure Regulator B | Mean-square Radius of Gyration (nm) | Melt Viscosity (Pa · s) | Thermal Stable Temperature (° C.) | Injection Molding Grade |
|---|---|---|---|---|---|---|---|
| Comparative 1 | Lauryl alcohol | — | — | 65 | 1200 | 268 | C |
| Polymer 1 | — | Glycidol | — | 28 | 192 | 251 | B |
| Polymer 2 | — | Glycidol | hexamethylene diisocyanate | 47 | 270 | 296 | A |

As shown in Table 1, the addition of the structure regulator A and the structure regulator B effectively reduced the melt viscosity and improved thermal stability of the resulting polymer, which was more suitable for processing into a polymer product.

Example 2. Polymers 3-21

Polymers 3-21 were prepared according to an integrated production process of polymerization, modification and processing. Each polymer was continuously produced for about 100 kg. In Example 2, the amounts of the catalyst and the end-capping agent and the relevant parameters for each process step were adjusted and the resulting polymers were tested for their monomer conversion rate, mean-square radius of gyration and melt viscosity.

Glycolide, tin tetrachloride or (ring-opening polymerization catalyst) in different amounts, and glycidol in an amount of 0.05 wt % parts relative to the weight of the glycolide were uniformly mixed in a prefabricated kettle reactor at a temperature T1 for a reaction time of t1. The material of the prepolymerization kettle reactor was transferred into a polymerization reactor. Hexamethylene diisocyanate in an amount of 0.1 wt % parts by weight relative to the weight of the glycolide was added. The polymerization was carried out at a temperature T2 under an absolute pressure P1. The polymerization reactor may be a plug flow reactor, which may be a static mixer, a twin screw unit or a horizontal disk reactor. The material in the polymerization reactor was then transferred into an optimized reactor. An end-capping agent in different amounts relative to the glycolide was added. The optimization reaction was carried out at a certain mixing speed and at a temperature T3 under an absolute pressure of P3 for a reaction time of t3. Finally, granulation wss carried out.

Example 3. Polymers 22-37

Polymers 22-37 were an integrated production process of polymerization, modification and processing. Each polymer was produced at about 100 kg continuously. In Example 3, the type and amount of a structure regulator were adjusted and the resulting polymers were tested for their mean-square radius of gyration, melt viscosity, thermal stable temperature and injection molding grade.

Glycolide, 0.05 wt % tin tetrachloride (ring-opening polymerization catalyst) and a structure regulator A in an amount of 0.05 wt % relative to the weight of the glycolide were mixed uniformly in a prepolymerization kettle reactor at 120° C. for 60 min. The material in the prepolymerization kettle reactor was transferred into a polymerization reactor. A certain amount of a structure regulator B was added. The polymerization reaction was carried out at 200° C. under an absolute pressure of 0.1 MPa for 300 min. The polymerization reaction may be a plug flow reactor, which may be a static mixer, a twin screw unit or a horizontal disk reactor. The material in the polymerization reactor was transferred into an optimization reactor. Dicyclohexylcarbodiimide (end-capping agent) in an amount of 0.2 wt % relative to the glycolide was added and mixed at 200 RPM at 220° C. under an absolute pressure of 50 Pa for 30 min. Finally, granulation was carried out.

Although the invention is illustrated and described herein with reference to specific embodiments, the invention is not intended to be limited to the details shown. Rather, various modifications may be made in the details within the scope and range of equivalents of the claims without departing from the invention.

TABLE 2

Polymers 3 and 21

| | Catalyst | Catalyst/Monomer (%) | T1 (° C.) | t1 (min) | T2/ (° C.) | t2 (min) | P2 (MPa) | End-Capping Agent | End-Capping Agent/Monomer (%) |
|---|---|---|---|---|---|---|---|---|---|
| Polymer 3 | Tin tetrachloride | 0.05 | 120 | 60 | 200 | 300 | 0.1 | Dicyclohexyl-carbodiimide | 0.2 |
| Polymer 4 | Tin tetrachloride | 0.01 | 120 | 60 | 200 | 300 | 0.1 | Dicyclohexyl-carbodiimide | 0.2 |
| Polymer 5 | Tin tetrachloride | 0.1 | 120 | 60 | 200 | 300 | 0.1 | Dicyclohexyl-carbodiimide | 0.2 |
| Polymer 6 | Stannous octoate | 0.01 | 120 | 60 | 200 | 300 | 0.1 | Dicyclohexyl-carbodiimide | 0.2 |
| Polymer 7 | Stannous octoate | 0.1 | 120 | 60 | 200 | 300 | 0.1 | Dicyclohexyl-carbodiimide | 0.2 |
| Polymer 8 | Tin tetrachloride | 0.05 | 180 | 10 | 200 | 300 | 0.1 | Dicyclohexyl-carbodiimide | 0.2 |
| Polymer 9 | Tin tetrachloride | 0.05 | 120 | 180 | 200 | 300 | 0.1 | Dicyclohexyl-carbodiimide | 0.2 |
| Polymer 10 | Tin tetrachloride | 0.05 | 120 | 60 | 190 | 1440 | 0.1 | Dicyclohexyl-carbodiimide | 0.2 |
| Polymer 11 | Tin tetrachloride | 0.05 | 120 | 60 | 220 | 10 | 0.1 | Dicyclohexyl-carbodiimide | 0.2 |
| Polymer 12 | Tin tetrachloride | 0.05 | 120 | 60 | 200 | 300 | 0.01 | Dicyclohexyl-carbodiimide | 0.2 |
| Polymer 13 | Tin tetrachloride | 0.05 | 120 | 60 | 200 | 300 | 0.1 | Dicyclohexyl-carbodiimide | 0.1 |
| Polymer 14 | Tin tetrachloride | 0.05 | 120 | 60 | 200 | 300 | 0.1 | Dicyclohexyl-carbodiimide | 1 |
| Polymer 15 | Tin tetrachloride | 0.05 | 120 | 60 | 200 | 300 | 0.1 | Diisopropyl-carbodiimide | 0.1 |
| Polymer 16 | Tin tetrachloride | 0.05 | 120 | 60 | 200 | 300 | 0.1 | Diisopropyl-carbodiimide | 1 |
| Polymer 17 | Tin tetrachloride | 0.05 | 120 | 60 | 200 | 300 | 0.1 | Dicyclohexyl-carbodiimide | 0.2 |
| Polymer 18 | Tin tetrachloride | 0.05 | 120 | 60 | 200 | 300 | 0.1 | Dicyclohexyl-carbodiimide | 0.2 |
| Polymer 19 | Tin tetrachloride | 0.05 | 120 | 60 | 200 | 300 | 0.1 | Dicyclohexyl-carbodiimide | 0.2 |
| Polymer 20 | Tin tetrachloride | 0.05 | 120 | 60 | 200 | 300 | 0.1 | Dicyclohexyl-carbodiimide | 0.2 |
| Polymer 21 | Tin tetrachloride | 0.05 | 120 | 60 | 200 | 300 | 0.1 | Dicyclohexyl-carbodiimide | 0.2 |

| | T3 (° C.) | t3 (min) | Mixing Speed (RPM) | P3 (Pa) | Monomer Conversion Rate (%) | Mean-square Radius of Gyration (nm) | Melt Viscosity (Pa · s) |
|---|---|---|---|---|---|---|---|
| Polymer 3 | 220 | 30 | 200 | 50 | 95 | 42 | 310 |
| Polymer 4 | 220 | 30 | 200 | 50 | 90 | 73 | 840 |
| Polymer 5 | 220 | 30 | 200 | 50 | 98.5 | 27 | 57 |
| Polymer 6 | 220 | 30 | 200 | 50 | 91 | 67 | 770 |
| Polymer 7 | 220 | 30 | 200 | 50 | 99 | 19 | 45 |
| Polymer 8 | 220 | 30 | 200 | 50 | 91.5 | 45 | 210 |

TABLE 2-continued

Polymers 3 and 21

| | | | | | | | |
|---|---|---|---|---|---|---|---|
| Polymer 9  | 220 | 30  | 200 | 50  | 94.5 | 55 | 320 |
| Polymer 10 | 220 | 30  | 200 | 50  | 93   | 61 | 960 |
| Polymer 11 | 220 | 30  | 200 | 50  | 89.5 | 35 | 250 |
| Polymer 12 | 220 | 30  | 200 | 50  | 92   | 41 | 290 |
| Polymer 13 | 220 | 30  | 200 | 50  | 94.5 | 43 | 340 |
| Polymer 14 | 220 | 30  | 200 | 50  | 95   | 48 | 310 |
| Polymer 15 | 220 | 30  | 200 | 50  | 95   | 40 | 370 |
| Polymer 16 | 220 | 30  | 200 | 50  | 96   | 51 | 290 |
| Polymer 17 | 230 | 10  | 200 | 50  | 96   | 49 | 410 |
| Polymer 18 | 190 | 360 | 200 | 50  | 97   | 46 | 360 |
| Polymer 19 | 220 | 30  | 50  | 50  | 94   | 47 | 330 |
| Polymer 20 | 220 | 30  | 200 | 1   | 92   | 48 | 310 |
| Polymer 21 | 220 | 30  | 200 | 100 | 96.5 | 48 | 320 |

TABLE 3

Polymers 22 and 37

| | Structure Regulator A | Structure Regulator A/Monomer (%) | Structure Regulator B | Structure Regulator B/Monomer (%) | Mean-square Radius of Gyration (nm) | Melt Viscosity (Pa · s) | Thermal Stable Temperature (° C.) | Injection Molding Grade |
|---|---|---|---|---|---|---|---|---|
| Polymer 22 | Trimethylolethane | 0.01 | Hexamethylene diisocyanate | 0.1 | 67 | 510 | 288 | A |
| Polymer 23 | Trimethylolethane | 1 | Hexamethylene diisocyanate | 0.1 | 23 | 67 | 258 | A |
| Polymer 24 | Trimethylolpropane | 0.01 | Hexamethylene diisocyanate | 0.1 | 61 | 430 | 293 | A |
| Polymer 25 | Trimethylolpropane | 1 | Hexamethylene diisocyanate | 0.1 | 25 | 73 | 287 | A |
| Polymer 26 | Pentaerythritol | 0.01 | Hexamethylene diisocyanate | 0.1 | 61 | 370 | 297 | A |
| Polymer 27 | Pentaerythritol | 1 | Hexamethylene diisocyanate | 0.1 | 25 | 69 | 271 | Thermal Decomposition |
| Polymer 28 | 3-methyl-3-hydroxymethyl-oxetane | 0.01 | Hexamethylene diisocyanate | 0.1 | 70 | 560 | 293 | B |
| Polymer 29 | 3-methyl-3-hydroxymethyl-oxetane | 1 | Hexamethylene diisocyanate | 0.1 | 28 | 110 | 295 | A |
| Polymer 30 | 3-ethyl-3-hydroxymethyl-oxetane | 0.01 | Hexamethylene diisocyanate | 0.1 | 71 | 550 | 293 | B |
| Polymer 31 | 3-ethyl-3-hydroxymethyl-oxetane | 1 | Hexamethylene diisocyanate | 0.1 | 27 | 120 | 297 | A |
| Polymer 32 | Glycidol | 0.01 | Hexamethylene diisocyanate | 0.1 | 66 | 470 | 287 | A |
| Polymer 33 | Glycidol | 1 | Hexamethylene diisocyanate | 0.1 | 17 | 45 | 258 | Thermal Decomposition |
| Polymer 34 | Glycidol | 0.05 | 2,2'-bis(2-oxazoline) | 0.01 | 31 | 250 | 278 | A |
| Polymer 35 | Glycidol | 0.05 | 2,2'-bis(2-oxazoline) | 1 | 74 | 570 | 294 | B |
| Polymer 36 | Glycidol | 0.05 | Hexamethylene diisocyanate | 0.01 | 35 | 290 | 280 | A |
| Polymer 37 | Glycidol | 0.05 | Hexamethylene diisocyanate | 1 | 66 | 490 | 297 | A |

What is claimed:

1. A polymer resin comprising one or more repeating units of —(—OCH₂—CO—)— or —(—CO—CH₂O—)— and one or more bonding units each selected from the group consisting of:

(a) bonding unit 1 is,

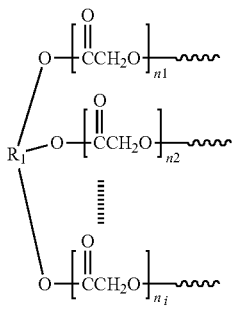

(b) bonding unit 2 is

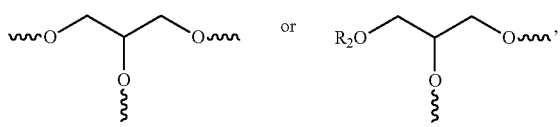

(c) bonding unit 3 is

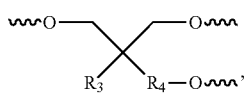

(d) bonding unit 4 is

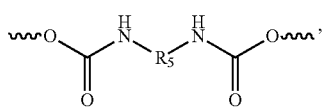

and
(e) bonding unit 5 is

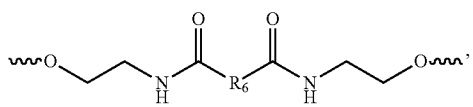

wherein ⁓⁓⁓ is a polymer segment consisting of a plurality of the repeating unit of —(—OCH₂—CO—)— or —(—CO—CH₂O—)—; R1, R2, R3, R4, R5 and R6 are each an aliphatic or aromatic group;
wherein bonding unit (a) has 3-20 arms, and each arm (i.e., each of $n_1, n_2 \ldots n_i$) may have 1-2,000, preferably 10-1,000, repeating units of —(—OCH₂—CO—)— or —(—CO—CH₂O—)—;
wherein each bonding unit is linked with a repeating unit or another bonding unit via covalent bond; and
wherein the polymer resin has a mean-square radius of gyration of 10-80 nm as measured in hexafluoroisopropanol at 25° C.;
the polymer resin is prepared by a process comprising the following:
(a) mixing glycolide with a catalyst, an initiator and a structure regulator A in a prepolymerization reactor at a temperature above the melting temperature of the glycolide and below the melting temperature of the polymer resin, whereby a melted prepolymerization composition is formed;
(b) polymerizing the melted prepolymerization composition in the presence of a structure regulator B, whereby a melted polymerization composition is formed; and
(c) devolatilizing and modifying the melted polymerization composition, whereby the melted PGA resin is formed.

2. The polymer resin of claim 1, wherein
the structure regulator A has the structural formula of $M_x$-R—$N_y$ ($2 \leq x+y \leq 20$), wherein M and N are each —OH, epoxy or oxetane, and R is an aliphatic or aromatic group; and,
the structure regulator B has the structural formula of $M_x$-R—$N_y$ ($2 \leq x+y \leq 20$), wherein M and N are each —N=C=O or oxazoline, and R is an aliphatic or aromatic group.

3. The polymer resin of claim 1, wherein the polymer resin is prepared by ring-opening polymerization of the glycolide in a molten state in the presence of the structure regulator A, the structure regulator B, and an end-capping agent.

4. The polymer resin of claim 3, wherein the end-capping agent is a carbodiimide compound.

5. The polymer resin of claim 1, wherein the polymer resin has a property selected from the group consisting of:
(a) a melt viscosity of 30-1200 Pa·s at a temperature of 225° C. and a shear rate 100 s⁻¹,
(b) a heat stable temperature above 280° C.,
(c) Grade A of injection molding grade at 240° C., and
(d) a combination thereof.

6. A process of preparing the polymer resin of claim 1, comprising ring-opening polymerizing the glycolide in a molten state in the presence of the structure regulator A and the structure regulator B.

7. A process of preparing the polymer resin of claim 1, comprising ring-opening polymerizing the glycolide in a molten state in the presence of the structure regulator A, the structure regulator B, and an end-capping agent.

8. A process of preparing the polymer resin of claim 1, comprising
(a) mixing the glycolide with a catalyst, the initiator and the structure regulator A in the prepolymerization reactor at the temperature above the melting temperature of the glycolide and below the melting temperature of the polymer resin, whereby the melted prepolymerization composition is formed;
(b) polymerizing the melted prepolymerization composition in the presence of the structure regulator B, whereby the melted polymerization composition is formed; and
(c) devolatilizing and modifying the melted polymerization composition, whereby the melted PGA resin is formed.

9. The process of claim 8, further comprising molding the melted polymer resin to make a PGA product.

10. The process of claim 6, wherein
the structure regulator A has the structural formula of $M_x$-R—$N_y$ ($2 \leq x+y \leq 20$), wherein M and N are each —OH, epoxy or oxetane, and R is an aliphatic or aromatic group; and, the structure regulator B has the structural formula of $M_x\text{-R-}N_y$ (2≤x+y≤20), wherein M and N are each —N=C=O or oxazoline, and R is an aliphatic or aromatic group.

11. The process of claim 7, wherein the end-capping agent is a carbodiimide compound.

\* \* \* \* \*